(12) United States Patent
Hsu et al.

(10) Patent No.: US 8,907,112 B2
(45) Date of Patent: Dec. 9, 2014

(54) METHOD FOR PREPARING EPOXIDE

(71) Applicant: China Petrochemical Development Corporation, Taipei (Taiwan), Taipei (TW)

(72) Inventors: Yu-Chuan Hsu, Taipei (TW); Cheng-Fa Hsieh, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 14/103,230

(22) Filed: Dec. 11, 2013

(65) Prior Publication Data

US 2014/0179938 A1    Jun. 26, 2014

(30) Foreign Application Priority Data

Dec. 26, 2012 (TW) .............................. 101150050 A

(51) Int. Cl.
*C07D 301/12* (2006.01)
*C07D 301/06* (2006.01)

(52) U.S. Cl.
CPC .................................. *C07D 301/12* (2013.01)
USPC .......................................... 549/531; 549/533

(58) Field of Classification Search
CPC ........................................................ C07D 301/12
USPC ................................................... 549/531, 533
See application file for complete search history.

(56) References Cited

U.S. PATENT DOCUMENTS

| | | |
|---|---|---|
| 4,824,976 A | 4/1989 | Clerici et al. |
| 4,937,216 A | 6/1990 | Clerici et al. |
| 5,646,314 A | 7/1997 | Crocco et al. |
| 5,675,026 A | 10/1997 | Thiele |

*Primary Examiner* — T. Victor Oh
(74) *Attorney, Agent, or Firm* — Edwards Wildman Palmer LLP; Peter F. Corless; Richard B. Emmons

(57) ABSTRACT

A method for producing an epoxide is disclosed. The method includes performing a reaction of an olefin compound and an oxidant by using a titanium-silicon molecular sieve as a catalyst, in the presence of a silicon oxide containing an alkaline earth metal as a coagent. The selectivity and yield of epoxide are increased by using a silicon oxide containing an alkaline metal as a coagent.

16 Claims, No Drawings

METHOD FOR PREPARING EPOXIDE

CROSS-REFERENCES TO RELATED APPLICATIONS

This application claims under 35 U.S.C. §119(a) the benefit of Taiwanese Application No. 101150050, filed Dec. 26, 2012, the entire contents of which is incorporated herein by reference.

BACKGROUND OF THE INVENTION

1. Field of the Invention

The present invention relates to a method of producing epoxide by performing epoxidation of an olefin compound. In particular, the present application relates to a method for preparing an epoxide by using a molecular sieve as a catalyst.

2. Description of Related Art

Methods of producing an epoxide include an epichlorohydrin method, a co-oxidation method, a direct oxidation method and the like. The epichlorohydrin method produces chlorine waste, which causes damage to the environment. The co-oxidation method involves complex procedures, with various co-products. The direct oxidation method can be divided into a direct oxidation by oxygen and a direct oxidation by peroxide. The direct oxidation method by oxygen produces an epoxide by using pure oxygen as a reactant, is simple and produces no intermediate. However, the direct oxidation method by oxygen has lower selectivity of products. Therefore, the direct oxidation method by peroxide is widely used. In the direct oxidation method by peroxide, a titanium-silicon molecular sieve is generally used as a catalyst, and the catalyst is easily separated from products. The direct oxidation method by peroxide would not cause damages to the environment, and not consume large amounts of oxygen. However, the epoxide selectivity and production rate of the direct oxidation method by peroxide still need to be improved.

U.S. Pat. No. 4,824,976, U.S. Pat. No. 4,937,216, U.S. Pat. No. 5,646,314 and U.S. Pat. No. 5,675,026 disclose the production of an epoxide by performing the direct epoxidation of olefin compounds using a titanium-silicon molecular sieve as a catalyst. In order to increase the selectivity and yield of epoxide, a coagent such as aqueous alkaline, non-alkaline (neutral and acidic) carboxylate, alcohols, halides, nitrates or phosphates of alkali metals or alkaline-earth metals can be added before the reaction, during the reaction, or before and during the reaction.

Although the addition of the aforementioned coagent during the method of producing an epoxide can increase the selectivity rate and yield of epoxide, the practical use of the additive results in many defects. For example, alkali metal ions and alkaline earth metal ions reduce the conversion rate of hydrogen peroxide; another example of defect is that the reactivity and the solubility of the additive influence the selectivity of epoxide. Further, the reaction system needs extra water content, which leads to an increase in the formation of by-products. Moreover, the isolation of the additive needs increased energy consumption, the additive that contains $H^+$ ions results in corrosion of equipment; and the presence of additives containing fluorine ions would destroy the structure of catalyst.

Therefore, there is a need to provide a substance for improving selectivity and yield of epoxide without the aforementioned defects.

SUMMARY OF THE INVENTION

The present invention provides a method of producing an epoxide. The method includes performing a reaction of an olefin compound and an oxidant by using a titanium-silicon molecular sieve as a catalyst, in the presence of a silicon oxide containing an alkaline earth metal as a coagent.

The catalyst has the structure of formula (I):

$$x\text{TiO}_2(1-x)\text{SiO}_2 \quad (I)$$

wherein x is in a range from 0.005 to 0.1.

The framework of the titanium-silicon molecular sieve has the structure of MFI, MEL, BEA, ZSM-48, MTW or MCM-41. The olefin compound is an organic compound containing at least one ethylene-based unsaturated functional group. The oxidant is any compound that produces or releases hydrogen peroxide in the epoxidation reaction.

The method of the present invention is suitable for use in any reaction vessel or equipment, such as fixed bed, transport bed, fluid bed, stirred slurry, or a continuous flow stirred tank reactor. The method of the present invention can also be used in a single-phase or two-phase systems, and can be performed in batches, continuously or semi-continuously.

In the method of the present invention, the amount of catalyst used is not strictly limited as long as the amount of the catalyst makes the epoxidation reaction completed in the shortest possible time. In one embodiment, the method of the present invention is performed in batches. Generally, 1 mole of the olefin compound and 0.001 to 10 g of the titanium-silicon molecular sieve are used. In another embodiment, the method of the present invention is performed in a fixed bed reactor. Generally, each kilogram of the catalyst required for the epoxidation reaction in the fixed bed reactor per hour is used for 1 to 100 moles of the olefin compound. In the whole epoxidation reaction, the concentration of titanium is usually maintained at 10 to 10,000 ppm.

The molar ratio of the olefin compound to the oxidant is in a range of from 1:100 to 100:1, and preferably in a range of from 1:10 to 10:1. The ratio amount of the coagent is in a range of from 0.15 to 15 wt % based on the amount of the catalyst.

The temperature at which the epoxidation reaction is performed is not particularly limited, but the epoxidation reaction is usually performed at a temperature in a range of from 0 to 150° C., and more preferably in a range of from 25 to 120° C. The reaction is performed for 1 minute to 48 hours, and preferably for 10 minutes to 8 hours. The method of the present invention can be performed under any pressure, but preferably under 1 to 100 atm, in order to increase the solubility of the gaseous reactants.

The method of the present invention is simple, and has high selectivity and yield of epoxide. As such, the method of the present invention has advantages in industrial applications.

DETAILED DESCRIPTION OF THE PREFERRED EMBODIMENTS

Specific embodiments are provided below to illustrate the methods of implementing the present invention. Persons skilled in the art can easily understand the advantages and effects of the present invention according to the disclosure of the specification of the present invention. The present invention can also be used in combination with different implementation methods. The details in the specification of the present invention can be based on different perspectives and applications without departing from the spirit of the present invention.

In the method of the present invention, the titanium-silicon molecular sieve in an anhydrous state has the structure of formula (I):

$$x\text{TiO}_2(1-x)\text{SiO}_2 \quad (I)$$

wherein x is in a range of from 0.005 to 0.1.

The titanium-silicon molecular sieve can be in the form of a powder, an agglomerate, a microsphere, a single block, extrusion molding, or any other form.

The titanium-silicon molecular sieve can optionally incorporate a transition metal or a heteroatom, via the co-condensation method, impregnation method, precipitation method, doping method, or other similar methods.

The silicon source of the titanium-silicon molecular sieve of the present invention may be, but not limited to, fumed silica ($SiO_2$), silica gel, silica sol, tetraalkyl silicate such as tetramethyl silicate, tetraethyl silicate, tetrapropyl silicate and tetrabutyl silicate. For example, the silica sol may be Ludox AS-40, Ludox AS-30, Ludox AM-30, Ludox TM-40, Ludox TM-50, Ludox AM-30, Ludox HS-30 and Ludox HS-40 of DuPont; or SNOWTEX-40, SNOWTEX-50, SNOWTEX-C, SNOWTEX-N, SNOWTEX-20L, SNOWTEX-ZL and SNOWTEX-UP of Nissan Chemical; or other similar products.

The titanium source of the titanium-silicon molecular sieve of the present invention may be, but not limited to, a titanium salt (for example, a titanium halide) or tetraalkyl titanate. In an embodiment of the present invention, the titanium source may be, but not limited to, at least one tetramethyl titanate, tetraethyl titanate, tetrapropyl titanate, tetra-n-butyl titanate, tetra-sec-butyl titanate, tetra-iso-butyl titanate and tetra-ter-butyl titanate.

The olefin compound used in the method of the present invention may be, but not limited to, at least an organic compound containing at least one vinyl unsaturated functional group (such as C=C), wherein the organic compound is cyclic, a branched, or straight chain. The organic compound may include an aromatic group.

In one embodiment, the olefin compound in the method of the present invention may be, but not limited to, $C_2$ to $C_{10}$ olefin compounds.

The olefin compound used in the method of the present invention may be, but not limited to, a monoolefin compound, wherein the monoolefin compound may be, but not limited to, ethylene, propylene, 1-butene, 2-butene, 1-pentene and cyclohexene.

In one embodiment of the present invention, the oxidant is hydrogen peroxide ($H_2O_2$). However, the hydrogen peroxide used is not limited to extra addition of hydrogen peroxide, but may be different compounds that can produce or release hydrogen peroxide. For example, when using the titanium-silicon molecular sieve containing the impregnated transition metal as a catalyst, the hydrogen peroxide is generated in situ. For instance, hydrogen peroxide is produced by introducing hydrogen and oxygen gas into the epoxidation reactor containing the titanium-silicon molecular sieve having the impregnated transition metal (such as palladium, platinum). In this example, no extra addition of hydrogen peroxide is necessary.

The coagent used in the method of the present invention is silicon oxide containing an alkaline earth metal which may be, but not limited to, magnesium silicon oxide (such as $MgSiO_3$, $Mg_2Si_3O_8$), calcium silicon oxide ($CaSiO_3$), strontium silicon oxide (such as $SrSiO_3$), or barium silicon oxide (such as $BaSiO_3$). The coagent can be added before the epoxidation reaction, during the reaction, or before and during the reaction. Also, the coagent can be added to the reactor system before the reaction, or added to the system during the reaction; or, the coagent can be added at different time points both before and during the reaction (that is, there can be at least two additions).

In the method of the present invention, a solvent can be added. The solvent is added to solubilize reactants other than the titanium-silicon molecular sieve, and to provide better temperature control. In order to increase the speed and selectivity of the epoxidation reaction, the amount of the solvent is in a range of from 1% to 99% based on the total weight of the reactants. Further, the solvent is in the liquid state at the temperature of the epoxidation reaction.

In the method of the present invention, the solvent may be, but not limited to, ketones, ethers, aliphatic compounds, aromatic hydrocarbon, halogenated hydrocarbon, $C_1$-$C_5$ alcohols, water or excess olefin compounds. Moreover, the presence of water does not have any negative effects (significant negative impact) on the epoxidation reaction. For example, using aqueous solution of hydrogen peroxide in the method of the present invention will not reduce the production of epoxide.

The following embodiments are to further demonstrate the methods of the present invention, and thus persons skilled in the art can understand the other advantages and effects of the present invention according to the disclosure of the present invention. However, the present invention is not limited to these embodiments.

Preparation of Titanium-Silicon Molecular Sieve

The titanium-silicon molecular sieve may be prepared by the method disclosed in U.S. Pat. No. 4,410,501, wherein the molar ratio of titanium to silicon is 0.027 (x is approximately 0.0277).

Comparative Example 1

This comparative example demonstrates the production of epoxide in olefin epoxidation reaction, wherein no coagent was added. 3 grams (g) of the titanium-silicon molecular sieve and 500 g of methanol were mixed well in a 1-liter autoclave. Gas pressure was built to 2 kg/cm$^2$ by using propylene gas, and the reaction was maintained at 40° C. This was followed by adding 16.23 g of hydrogen peroxide (35 wt %) at a feeding rate of 1 ml per minute to the mixture, and propylene gas was used to maintain the pressure at 2 kg/cm$^2$. After completion of feeding of hydrogen peroxide, the reaction solution was removed. Iodine titration analysis was performed to analyze the conversion rate of hydrogen peroxide, and the concentration of each product was analyzed by gas chromatography. The results are shown in Table 1.

Embodiments 1 to 5 Comparisons of Different Amounts of Coagents

These embodiments demonstrate epoxide is prepared by performing epoxidation of olefin compounds with a coagent, which is a silicon oxide containing an alkaline earth metal.

The reaction conditions in these embodiments were similar to those in Comparative Example 1 except that before the epoxidation reaction was performed, different amounts of $MgSiO_3$ were added. 0.07 g of $MgSiO_3$ was added in Embodiment 1, 0.17 g of $MgSiO_3$ was added in Embodiment 2, 0.26 g of $MgSiO_3$ was added in Embodiment 3, 0.32 g of $MgSiO_3$ was added in Embodiment 4, and 0.38 g of $MgSiO_3$ was added in Embodiment 5, respectively. Also, the reactants and the coagent were stirred for 30 minutes such that the coagent was well dispersed in the mixture of the reactants. The results of the reactions in these embodiments are shown in Table 1.

Embodiments 6 to 8 Comparisons Between Different Coagents

These embodiments demonstrate the production of epoxide by epoxidation of olefin compounds by using different silicon oxide coagents containing alkaline earth metals.

The reaction conditions in these embodiments were similar to those for Comparative Example 1 except that before the epoxidation reaction was performed, various coagents were respectively added as follows. 0.03 g of $Mg_2Si_3O_8$ was added in Embodiment 6, 0.12 g of $CaSiO_3$ was added in Embodiment 7, and 0.11 g of $BaSiO_3$ was added in Embodiment 8. Also, the reactants and the coagent were stirred for 30 minutes such that the coagent was well dispersed in the mixture of the reactants. The reaction results of these embodiments are shown in Table 1.

TABLE 1

| Embodiments | Coagent | Amount added (g) | $X_{H2O2}$ (%) | $S_{PO}$ (%) | $Y_{PO}$ (%) |
|---|---|---|---|---|---|
| Comparative Example 1 | — | — | 99.5 | 89.1 | 88.6 |
| Embodiment 1 | $MgSiO_3$ | 0.07 | 99.7 | 91.6 | 91.3 |
| Embodiment 2 | $MgSiO_3$ | 0.17 | 99.4 | 94.1 | 93.6 |
| Embodiment 3 | $MgSiO_3$ | 0.26 | 98.9 | 95.1 | 94.0 |
| Embodiment 4 | $MgSiO_3$ | 0.32 | 96.8 | 95.1 | 92.1 |
| Embodiment 5 | $MgSiO_3$ | 0.38 | 94.9 | 95.4 | 90.5 |
| Embodiment 6 | $Mg_2Si_3O_8$ | 0.03 | 99.4 | 93.4 | 92.9 |
| Embodiment 7 | $CaSiO_3$ | 0.12 | 99.5 | 93.9 | 93.4 |
| Embodiment 8 | $BaSiO_3$ | 0.11 | 99.1 | 94.8 | 93.9 |

The coagent was obtained from Sigma-Aldrich Corporation.
$X_{H2O2}$ = conversion rate of hydrogen peroxide = number of moles of consumed hydrogen peroxide/the total number of moles of hydrogen peroxide × 100%;
$S_{PO}$ = selectivity of epoxypropane = number of moles of generated epoxypropane/number of moles of consumed hydrogen peroxide × 100%;
$Y_{PO}$ = the yield of epoxypropane = number of moles of generated epoxypropane/the total number of moles of hydrogen peroxide × 100%.

As shown in Table 1, in comparison with Comparative Example 1, the addition of the silicon oxide coagent containing the alkaline earth metal in Embodiments 1 to 8 significantly increases the selectivity and yield of epoxypropane, in which the conversion rate of hydrogen peroxide is higher than 99%. In addition, in comparison with Comparative Example 1, Embodiments 1 to 5 of the present invention showed that different amounts of $MgSiO_3$ were added to increase the yield of epoxypropane.

The method of the present invention achieves higher selectivity and yield of epoxypropane while substantially increasing production efficiency.

The above embodiments have only shown the theories and effects of the present invention, and they are not intended to limit the present invention. Persons skilled in the art may modify the above mentioned embodiments without violating and departing from the spirit and claim scope of the present invention. Therefore, the claims of the present invention should be interpreted as listed in the claims section below.

What is claimed is:

1. A method for preparing an epoxide, comprising the step of:
performing a reaction of an olefin compound and an oxidant by using a titanium-silicon molecular sieve as a catalyst, in the presence of a silicon oxide containing an alkaline earth metal as a coagent, wherein the titanium-silicon molecular sieve comprises a transition metal, and wherein the silicon oxide containing an alkaline earth metal is at least one selected from the group consisting of $MgSiO_3$, $Mg_2Si_3O_8$, $CaSiO_3$, $SrSiO_3$ and $BaSiO_3$, and the coagent is well dispersed in the olefin compound and the oxidant.

2. The method of claim 1, wherein the coagent is added before the reaction, during the reaction or before and during the reaction.

3. The method of claim 1, wherein an amount of the coagent is in a range of from 0.1 to 15 wt % based on an amount of the titanium-silicon molecular sieve.

4. The method of claim 1, wherein the titanium-silicon molecular sieve has a structure of formula (I):

$$xTiO_2(1-x)SiO_2 \qquad (I)$$

wherein x is in a range of from 0.005 to 0.1.

5. The method of claim 1, wherein a framework of the titanium-silicon molecular sieve is a structure of MFI, MEL, BEA, ZSM-48, MTW or MCM-41.

6. The method of claim 1, wherein the titanium silicon molecular sieve comprises a transition metal.

7. The method of claim 1, wherein a molar ratio of the olefin compound to the oxidant is in a range of from 1:100 to 100:1.

8. The method of claim 1, wherein the olefin compound is selected from $C_2$ to $C_{10}$ olefin compounds.

9. The method of claim 7, wherein the olefin compound is a monoolefin compound.

10. The method of claim 9, wherein the single-olefin compound is ethylene, propylene, 1-butene, 2-butene, 1-pentene, or cyclohexene.

11. The method of claim 9, wherein a molar ratio of the single-olefin compound to the oxidant is in a range of from 1:10 to 10:1.

12. The method of claim 1, wherein the oxidant is hydrogen peroxide.

13. The method of claim 1, wherein a solvent is added in the reaction, and the solvent is water, $C_1$ to $C_5$ alcohol, or a combination thereof.

14. The method of claim 13, wherein the solvent is methanol.

15. The method of claim 1, wherein the reaction is performed at a temperature in a range of from 0 to 150° C.

16. The method of claim 15, wherein the reaction is performed at a temperature in a range of from 25 to 120° C.

* * * * *